(12) United States Patent
Johnstone (10) Patent No.: US 9,216,036 B2
(45) Date of Patent: Dec. 22, 2015

(54) TISSUE ANCHOR INSERTION SYSTEM

(75) Inventor: Alan John Johnstone, Aberdeen (GB)

(73) Assignee: The Robert Gordon University, Aberdeen (GB)

( * ) Notice: Subject to any disclaimer, the term of this patent is extended or adjusted under 35 U.S.C. 154(b) by 915 days.

(21) Appl. No.: 13/258,667

(22) PCT Filed: Apr. 23, 2010

(86) PCT No.: PCT/GB2010/050660
§ 371 (c)(1),
(2), (4) Date: Nov. 1, 2011

(87) PCT Pub. No.: WO2010/122345
PCT Pub. Date: Oct. 28, 2010

(65) Prior Publication Data
US 2012/0041454 A1  Feb. 16, 2012

(30) Foreign Application Priority Data

Apr. 24, 2009  (GB) .................................. 0907064.0

(51) Int. Cl.
*A61B 17/10*   (2006.01)
*A61B 17/34*   (2006.01)
*A61B 17/04*   (2006.01)
*A61B 17/16*   (2006.01)
(Continued)

(52) U.S. Cl.
CPC ......... *A61B 17/3472* (2013.01); *A61B 17/0401* (2013.01); *A61B 17/1633* (2013.01); *A61B 2017/0046* (2013.01); *A61B 2017/0409* (2013.01); *A61B 2017/0417* (2013.01); *A61B 2019/304* (2013.01); *A61B 2019/462* (2013.01)

(58) Field of Classification Search
CPC .......... A61B 17/0401; A61B 17/1637; A61B 17/3417
USPC ......................................................... 606/232
See application file for complete search history.

(56) References Cited

U.S. PATENT DOCUMENTS 3,993,079 A * 11/1976 Henriques de Gatztanondo ............ 604/164.01
4,491,132 A *  1/1985 Aikins .......................... 606/170

(Continued)

FOREIGN PATENT DOCUMENTS

DE   102004012680 A1  11/2005
FR        2799635 A1   4/2001
WO  WO-2005/048885 A1   6/2005

OTHER PUBLICATIONS

Macaire, Stephane, "International Search Report" for PCT/GB2010/050660, as mailed Aug. 26, 2010, 6 pages.

*Primary Examiner* — Gregory Anderson
(74) *Attorney, Agent, or Firm* — Winstead PC (57) ABSTRACT

A tissue anchor insertion system for inserting a tissue anchor into a body tissue such as bone, comprising a cutting device having a sharp leading end to create an aperture in the bone for insertion of the tissue anchor therein. The cutting device is deployed through a sleeve which is a close fit with the cutting device. The distal end of the sleeve is typically configured to penetrate the tissue in which the tissue anchor is to be inserted. A tissue anchor is also deployed through the sleeve, after the sleeve is in position, on a delivery device configured to support the tissue anchor during its insertion into the tissue. Typically the leading end of the sleeve is embedded within the tissue when the tissue anchor emerges from the distal end during the insertion process, so the tissue anchor is not damaged by insertion through the tissue.

33 Claims, 4 Drawing Sheets

(51) Int. Cl.
   *A61B 17/00* (2006.01)
   *A61B 19/00* (2006.01)

(56) References Cited

U.S. PATENT DOCUMENTS 5,207,679 A * 5/1993 Li .................................. 606/232
5,275,611 A * 1/1994 Behl .............................. 606/198
5,441,502 A * 8/1995 Bartlett ......................... 606/104
5,484,437 A * 1/1996 Michelson .................. 606/86 A
6,080,174 A * 6/2000 Dubrul et al. ................. 606/185
2002/0193830 A1 12/2002 Bonutti
2008/0058816 A1 3/2008 Philippon et al.
2008/0188854 A1 8/2008 Moser

* cited by examiner

TISSUE ANCHOR INSERTION SYSTEM

This invention relates to a tissue anchor insertion system, for insertion of tissue anchors such as suture anchors into bone or cartilage or into other dense tissue, typically for anchorage of a suture, and to methods of its use.

Tissue anchors are widely used in surgery to retain and anchor sutures or other restraining devices in dense body tissues, so that the sutures or other restraining devices can be connected to other tissues. A common example is the use of a tissue anchor in bone to anchor one end of a suture so that the other end of the suture can be connected to a ligament, tendon or any other suturable soft tissue. Typically a hole is drilled into cortical bone (the dense outer layer of bone) creating a bore or tunnel optionally extending through the cortical bone, and a delivery probe is used to push the tissue anchor through the pre-drilled tunnel and typically into the cancellous layer (a less dense inner layer of bone). Some designs of toggle anchor are simply pushed through the tunnel by the probe and upon emergence from the distal end of the tunnel and withdrawal of the probe they rotate into a different configuration with can resist being pulled back through the tunnel. In some cases anchors are provided with screw threads to engage within the walls of the bore or tunnel in the cortical layer.

According to the present invention there is provided a tissue anchor insertion system for inserting a tissue anchor into a body tissue, the system comprising a cutting device having a sharp leading end configured to create an aperture in a body tissue for insertion of the tissue anchor therein, a sleeve having proximal and distal ends and having a bore through the sleeve, extending at least partially between the proximal and distal ends, and a tissue anchor delivery device configured to support the tissue anchor during insertion of the tissue anchor into the tissue, wherein during creation of the aperture in the tissue the cutting tool is adapted to be received within bore of the sleeve and is adapted to extend at least partially from a distal end of the bore at the distal end of the sleeve; wherein the distal end of the sleeve is configured to penetrate the tissue in which the tissue anchor is to be inserted; and wherein during insertion of the tissue anchor the sleeve is configured to accommodate the tissue anchor and the delivery device within the bore of the sleeve and to allow passage of the tissue anchor through the distal end of the bore.

Typically the distal end of the sleeve is configured to pass through the aperture created by the cutting device, so that the leading end of the sleeve is embedded within the tissue when the tissue anchor emerges from the distal end during the insertion process. Optionally the walls of the distal end have angled end faces (typically having the same angular deviation from the long axis of the sleeve as the leading end of the cutting device) so that the walls of the distal end of the sleeve form a substantially continuous slope with the leading end of the cutting device. The sleeve can optionally incorporate cutting formations to cut the tissue in which the tissue anchor is to be inserted. The sleeve can thereby cut part of the hole through the tissue. The sleeve can comprise a drill sleeve. The cutting formations can include teeth and/or spiral formations adapted to drill the aperture in the tissue. The walls of the leading end can typically converge to terminate in a sharp ridge at the distal tip of the sleeve configured to cut into the tissue. The sleeve can optionally be used to widen the aperture formed by the cutting device.

The outer surface of the sleeve can optionally be smooth to assist in the passage of the sleeve through the inner bore of a cannulated instrument.

The inner surface of the sleeve can optionally be smooth to reduce the tendency of the sutures to catch on the sleeve. The bore of the sleeve typically accommodates the suture, which is typically attached to the tissue anchor during insertion of the tissue anchor through the bore of the sleeve.

The cutting device can be an elongate rod with a sharpened drill bit or trocar tip. The sharpened leading end of the cutting device can have a tip with a plain needle point, a two or three or four sided trocar type tip, or can have a spiral formation to facilitate drilling or boring of the cutting device into the tissue upon rotation of the tip. The tip can be extended, with a leading pilot portion having walls with a narrower leading angle with respect to the longitudinal axis of the cutting device than a subsequent portion of the cutting device. The pilot portion is typically configured to pierce a pilot hole before a wider hole is created by the subsequent portion of the cutting device. The cutting device can optionally be asymmetrical. Typically the leading end of the tip of the cutting device can be asymmetrical.

Typically at least one of the cutting device and the sleeve has a shoulder to engage the other in order to transmit axial forces between the two components. The shoulder is typically located on the cutting device, facing the leading end thereof and typically engages an oppositely facing shoulder on the sleeve. The shoulder is typically located so that insertion of the cutting device into the bore of the sleeve and consequent engagement of the shoulder results in the sharp leading end of the cutting device protruding from the distal end of the sleeve by a defined extent sufficient to puncture the tissue, typically cortical bone. When the cutting device is then withdrawn form the sleeve, it therefore typically creates a void, which can be of defined proportions, distal to the end of the sleeve, to facilitate the deployment of the anchor. The dimensions of the void are determined by the shape of the tip of the cutting device and the distance that it extends out of the sleeve, which can be varied according to different designs of cutting device by using different diameters of tip on the cutting device, and positions of shoulder. The distance of the extension of the cutting device beyond the sleeve and the dimensions of the cutting device can be selected in accordance with different designs of anchor, to optimise the transition of the anchor between the insertion and the set configurations.

In some embodiments the delivery device can extend beyond the distal end of the sleeve, to space the anchor away from the distal end of the sleeve during configuration changes of the anchor in the tissue.

In some embodiments, the delivery device and/or the sleeve can have graduation marks indicating the depth of insertion of the anchor within the sleeve.

In some embodiments, the delivery device does not have a defined maximum depth of insertion into the sleeve, and optionally, the delivery device and/or the sleeve lack a step or shoulder. In such embodiments, the anchor can be supported in the sleeve by a rod which can slide within the sleeve. Optionally the rod can comprise a modified form of the delivery device. Such embodiments are useful to maintain support for the anchor during withdrawal of the sleeve from the tissue after the anchor has been inserted into the tissue. Also, such embodiments have an advantage that the anchor can be further manipulated or supported by the rod when the sutures are being moved or tensioned, and can keep the anchor spaced away from the end of the sleeve when the anchor is being set in the tissue. Therefore, the anchor and typically the sutures avoid the end of the sleeve during configuration changes of the anchor in the tissue and are less likely to be damaged by any of the cutting teeth or sharp end faces of the sleeve during the setting process.

Typically the cutting device and the sleeve are rotationally connected together in order to restrict relative movement of the components and allow or enhance the transmission of torque between the two components. For example, the two may be connected by a spline, or by one or more flats between the inner surface of the sleeve and the outer surface of the cutting device, which engage against one another to resist relative rotation between the two components when the cutting device is located within the sleeve. The rotational connection between the two components can be provided along the length of the sleeve or only at one end thereof, e.g. the distal leading end, or the proximal end. In some embodiments of the invention, the rotational connection can connect the two components in other ways, allowing transmission of e.g. axial movement between the components. For example, the connection can comprise a bayonet connection or a threaded connection or similar between the components, allowing transmission of rotational and axial movement between the components. In some embodiments, a rotational connection between the sleeve and the cutting device is unnecessary and/or undesirable. In some embodiments, the cutting device and sleeve can be inserted into the tissue by pushing with relatively moderate force, and in such embodiments, the cutting device can optionally be rotated by hand relative to the sleeve, which can optionally remain rotationally static in the tissue; such variations are useful in softer tissues. In certain embodiments, the cutting bit can be driven by a drill to rotate inside the sleeve, which can optionally remain rotationally static relative to the tissue.

Typically the cutting device can be a close fit within the bore of the sleeve, so that the inner wall of the sleeve is supported by the cutting device substantially along the whole bore of the sleeve. At least a part, e.g. the distal end of the tip of the sleeve can be supported by e.g. the cutting device being a close fit within the bore of the sleeve at the distal end thereof.

Optionally a portion of the cutting device can be formed with a flat or other feature to transmit torque applied by an operator, for example at the proximal trailing end of the cutting device, the shaft of the cutting device can optionally have a chuck engaging portion, such as a hexagonal head incorporating at least one flat to transmit torque applied by a the operator.

Optionally the sleeve can be slotted to permit passage of sutures through the slot, typically while retaining the delivery device within the bore.

Optionally the distal end of the sleeve can be toothed on its end face to cut into the tissue. The teeth can be regularly spaced or irregularly spaced. The teeth can optionally be arranged to cut preferentially in one direction, or can be arranged to cut in e.g. two directions, and in some embodiments of the invention, the toothed end face of the sleeve can be arranged to cut into the tissue by a reciprocating movement. The sleeve can optionally have an abrading formation on its outer surface and spaced away from the leading end. The abrading formation typically points toward the leading end, so that the outer surface of the aperture made by the sleeve is abraded by the formation. The abrading formation typically extends perpendicularly from an outer surface of the sleeve, and may have a radial component, but in some embodiments, the abrading formation can be formed on a shoulder of the sleeve, and can face the leading end, without having a radial component. The abrading formation can comprise at least one ridge. Typically the abrading formation comprises a series of ridges spaced circumferentially around the sleeve.

Typically the sleeve has an external formation such as a flange or a shoulder to limit the passage of the sleeve into the tissue. The abrading formation can be located on the external formation.

Optionally the cutting device has an external key or spline to engage the sleeve, and to allow transmission of torque between the two components. Typically the key or spline runs along at least a part of the length of the cutting device, and can usefully be configured to engage at least a part of the slot on the sleeve. In some embodiments, the open slot on the sleeve is optionally occluded along its length by the spline on the cutting device, which ameliorates damage to the tissue caused by the rotation of the slot during insertion of the sleeve into the tissue. At least one of the edges of the slot (optionally both) can be formed with an undercut, to reduce scraping damage to the tissues and damage to the sleeve upon rotation of the sleeve within the tissue.

In some embodiments, the cutting device can comprise an axial shaft, which can optionally have a cutting formation that extends radially with respect to the axial shaft. The cutting formation can optionally extend through the slot in the sleeve, and can optionally extend radially beyond than the outer surface of the sleeve, in order to cut into the tissue to form the aperture for passage of the sleeve and the cutting device into the tissue. The cutting formation can optionally be hardened. The cutting formation can optionally be provided at one end of the axial shaft, e.g. advantageously the leading end of the shaft, and in some embodiments can extend part or all of the way along the shaft. The cutting formation can optionally form part of the rotational connection between the cutting device and the sleeve.

Typically the cross section of the cutting device is a close fit with the bore of the sleeve so that when the sharp leading end of the cutting device protrudes from the distal end of the sleeve, the bore is substantially occluded by the cutting device, and the tissue being penetrated is thereby excluded from the bore of the sleeve.

In certain embodiments, the tissue anchor delivery device can optionally have an eccentric distal tip to engage the tissue anchor. Forming the delivery device with a eccentric tip to push the tissue anchor ahead of the delivery device through the sleeve means that the delivery device engages and pushes the anchor through the bore of a sleeve by means of a fulcrum; when the tissue anchor emerges from the distal end of the sleeve in the tissue, the eccentric tip no longer provides a stable support for the anchor, and this increases the tendency for the anchor to rotate in the tissue and change its orientation after passage through the sleeve. In typical embodiments, the anchor can be pushed down the sleeve in an "end-on" configuration with the portion of the anchor engaging the tip of the delivery device being a different shape to the delivery device in order to enhance rotation of the unsupported anchor after it emerges from the distal end of the sleeve.

In certain embodiments, the cross-sectional configuration of the delivery device can be different from the cross-sectional configuration of the sleeve. In some of these embodiments, one or more channels can be formed between the delivery device and the sleeve for accommodation of sutures in the channels, extending from the tissue anchor back through the sleeve. For example, where the internal bore of the sleeve has a circular cross section, the delivery device can have a shaft with one or more flats, e.g. one that is at least partially non-circular, for example triangular, square or hexagonal etc, so that one, two, three or more axial channels are defined between the inner surface of the circular bore of the sleeve and the outer surface of the square delivery device. The sutures trailing from the suture anchor through the sleeve can therefore be retained within the channels and can avoid being damaged by snagging between the sides of the delivery device and the sleeve.

In some embodiments of the invention, the delivery device and/or the anchor can have channels in its outer surface for accommodating sutures, and optionally can also or alternatively have formations configured for connection of the sutures to the delivery device and/or the anchor, for example cleats or hoops to assist in handling of the sutures on the delivery device and/or the anchor.

In some embodiments of the invention, the cutting device can optionally have a formation at its distal end to facilitate connection with a handle for manipulating the cutting device. The system can also incorporate a handle for connection to the cutting device. The connection between the handle and the cutting device can be configured for transferring axial and rotational forces between the handle and the cutting device. A suitable form of connection between the handle and the cutting device can optionally comprise a bayonet fitting (uni- or bi-directional) and/or a screw thread and/or a chuck device.

In some embodiments of the invention, the sleeve can optionally have a formation at its proximal end to facilitate connection with a handle for manipulating the sleeve. The system can also incorporate a handle for connection to the sleeve. The connection between the handle and the sleeve can be configured for transferring axial and rotational forces between the handle and the sleeve. A suitable form of connection between the handle and the sleeve can optionally comprise a bayonet fitting (uni- or bi-directional) and/or a screw thread and/or a chuck device. The same handle can be used for the sleeve and the cutting device.

In some embodiments of the invention, the cutting device can optionally incorporate a spike on its distal tip to stab into the tissue before rotation, in order to guide the cutting device and retain it in the same location during formation of the aperture through the tissue.

In some embodiments, the cutting device can be cannulated to receive a guide wire or other such guide device.

The invention also provides a method of inserting a tissue anchor into a tissue, the method comprising providing a cutting device having a sharp leading end configured to create an aperture in a body tissue for insertion of a tissue anchor therein, inserting the cutting device into the bore of a sleeve having an open end, inserting the cutting device and the open end of the sleeve into the tissue, typically to a depth at which the open end of the sleeve corresponds to the desired depth of insertion of the tissue anchor, mounting the tissue anchor on a delivery device and inserting the tissue anchor and the delivery device into the bore of the sleeve, and moving the delivery device relative to the sleeve to urge the tissue anchor out of the open end of the sleeve and into the surrounding tissue.

The tissue anchor does not need to be inserted through the tissue, and it is sufficient in some embodiments for the tissue anchor to be embedded within the tissue. In some embodiments, the tissue anchor can optionally be passed through interfaces between one tissue and another, for example crossing between cortical and cancellous bone to lodge in cancellous bone, beyond the cortical layer.

Typically the cutting device is removed from the bore prior to inserting the tissue anchor and the delivery device into the bore. Typically the sleeve remains in place in the tissue during removal of the cutting device and during insertion of the delivery device and the tissue anchor, and can typically be withdrawn from the tissue after the tissue anchor has been inserted. Typically the sleeve has a proximal and a distal end and typically the bore extends fully between the proximal and distal ends of the sleeve. The cutting device and the delivery device and the tissue anchor are typically initially inserted into the bore at the proximal end of the sleeve, and are typically passed through the bore from one end of the sleeve to the other before the cutting device and the tissue anchor emerge from the distal end. Thus the sleeve is inserted into the tissue and typically forms a work channel to facilitate access to the tissue or organ in which the anchor is to be implanted. The aperture for insertion of the system and the anchor is created at the same time that the work channel is established in a single step, and therefore the process of inserting the anchor through the work channel in the sleeve is much easier than inserting the anchor through a hole created in the bone. The anchor travels within the sleeve to its insertion point in the tissue and can thereby typically be maintained in an insertion configuration by the confines of the sleeve, thereby preventing the premature change of configuration into the set configuration during insertion. Typically there is a stop that limits the axial travel of the cutting device within the bore, so that the tip of the cutting device extends a defined distance from the distal end of the sleeve when the stop is engaged and therefore by engagement of the stop, an operator can tell that the tip of the cutting device is protruding by the defined distance from the distal end of the sleeve.

The cutting device and the sleeve and/or the anchor can optionally be formed of metal, typically a biocompatible metal such as stainless steel, titanium, cobalt chrome etc, or from a biocompatible plastics material such as PE, PEEK, PEK etc, or from a non-metallic material such as glass, ceramic material or polylactic acid etc. In some embodiments the anchor can be formed from a hydrophilic material that is adapted to swell when the anchor is inserted. A suitable material is disclosed in WO2005/048885, the contents of which are incorporated herein by reference. In some embodiments the anchor can be formed from a biocompatible plastics material adapted to dissolve over time in the insertion site, after the soft tissue suturing has been completed and the patient has healed.

The anchor can be adapted to change configurations between an insertion configuration in which the anchor can pass through the sleeve and a set configuration in which the anchor cannot pass through the sleeve. The insertion configuration is typically adopted during insertion and the set configuration is typically adopted after the anchor has been pushed out of the open end of the sleeve. In some embodiments, the anchor can be resilient.

The anchor can optionally be an asymmetric anchor. The anchor can optionally be adapted to change its shape after insertion. The anchor can be formed with expansion joints to mechanically alter its configuration after insertion to adopt the set configuration, or alternatively, or additionally, the anchor can be formed from material that is inherently adapted to change its shape after insertion of the anchor into the tissue, for example the anchor can be formed from a shape memory material or from expandable material.

The anchor can typically be attached to sutures and optionally to suture needles, although these can optionally be threaded onto the anchor prior to insertion. The anchor can typically be adapted to pass through the bore of the sleeve in a particular configuration, typically in the insertion configuration. The anchor can have a cross section that is adapted to fill the bore of the sleeve but may define axial channels in or past the anchor (e.g. through the anchor, in the outer surface of the anchor, or in the inner surface of the sleeve) for accommodating the sutures that are extending through the bore from the anchor to the proximal end of the sleeve. For example, for a circular bore, the anchor may have an oval cross section in the insertion configuration, whereby the sutures can be accommodated in the spaces between the bore and the minor diameter of the oval while the anchor is passing through the bore, while the major diameter substantially fills the bore and prevents the anchor from rotating while within the bore, thereby maintaining its insertion configuration while in the bore.

In one embodiment the anchor can be keyed to the bore of the sleeve, so as to maintain the insertion configuration of the anchor during insertion.

In one embodiment, the anchor can be longer than the width of the bore so that the anchor travels through the bore only in an end-on configuration, and the confines of the bore maintains the end on insertion configuration until the anchor emerges from the distal open end of the sleeve. The anchor can optionally have at least one end face that is urged by the delivery device during insertion. The end face that is urged can be angled at a different angle as compared with the portion of the delivery device that engages it, so that while the anchor is in the confines of the delivery sleeve, the end on configuration is maintained, but when the anchor emerges from the open end of the sleeve, the different angles between the delivery device and the anchor cause the anchor to change configuration from the insertion configuration to adopt the set configuration, and to resist re-insertion into the bore of the sleeve, or the aperture through the tissue. For example, in one embodiment, the end of the delivery sleeve can have a square end, perpendicular to the long axis of the bore, and the anchor can have a slanted end set at an oblique angle (e.g. 60 degrees) that is engaged by the delivery sleeve square end. Thus while the anchor is held within the confines of the bore, the tip of the oblique end is engaged by an edge of the square end, but the bore keeps the anchor and the delivery sleeve axially aligned with one another, but when the anchor emerges from the distal end of the bore, it is no longer held in axial alignment with the sleeve, and the oblique and square ends meet, causing rotation of the anchor, and changing the configuration from the insertion configuration into the set configuration, thereby preventing the return of the anchor through the bore. The square end can optionally be on the anchor, and the oblique end can be on the delivery device. Other angles and shapes can be used.

In one embodiment of the anchor the suture is attached to the anchor at an eccentric attachment point. Tensioning of the suture after emergence of the anchor from the bore of the sleeve typically facilitates change of the configuration of the anchor from the insertion configuration to the set configuration. This effect is typically enhanced by (but does not necessarily require) an eccentric suture connection to the anchor.

Optionally the sutures can be self tensioning.

Optionally the cutting device and/or the delivery device can be cannulated to permit the use of guide wires during insertion. In some embodiments the anchor can be cannulated.

Embodiments of the present invention will now be described by way of example, with reference to the accompanying drawings, in which.

Referring now to the drawings, a tissue anchor insertion system has a cutting device in the form of a drill stem 10 having a long axial shaft 11 with a distal end 10*d* having a cutting bit 12, and a proximal end 10*p* having with a flanged head 13. The cutting bit 12 has a sharpened tip in the form or a two sided trocar, but could also have spiral cutting formations adapted for rotary drilling. The cutting bit 12 is adapted to penetrate dense body tissue such as cortical and/or cancellous bone in which a tissue anchor 40 is to be anchored.

A sleeve of the present embodiment is provided in the form of a drill sleeve 20 having a main body 21 with a long axis about which the sleeve is generally symmetrical, and has a proximal end 20*p* and a distal end 20*d*. The drill sleeve 20 has a bore 25 providing a work channel between the outside of the patient's body, which is easily accessible by the operator, and the area of the tissue in which the anchor is to be implanted. The body 21 is connected to a neck 23 at the distal end 20*d* by means of a shoulder 22 that extends radially (either perpendicularly or, as is shown here, at an oblique angle to the long axis of the drill sleeve 20). The shoulder could optionally be a flange extending radially from a plain sleeve. At the distal end 20*d* of the sleeve, the neck 23 optionally terminates on its end face with a cutting formation in the form of an angled end face 24 best seen in FIG. 4. The angled end face 24 extends at an angle of around 60 degrees to the long axis of the drill sleeve 20, with the radially inner edge of the end face 24 extending further that the radially outer edge so that the distal tip of the end face is radially close to the axis. Optionally or additionally, the end face can have other types of cutting formation and could for example be toothed (not shown) and can thereby be adapted to drill or cut into the tissue in which the anchor is to be inserted.

Figures 1, 2, 3:
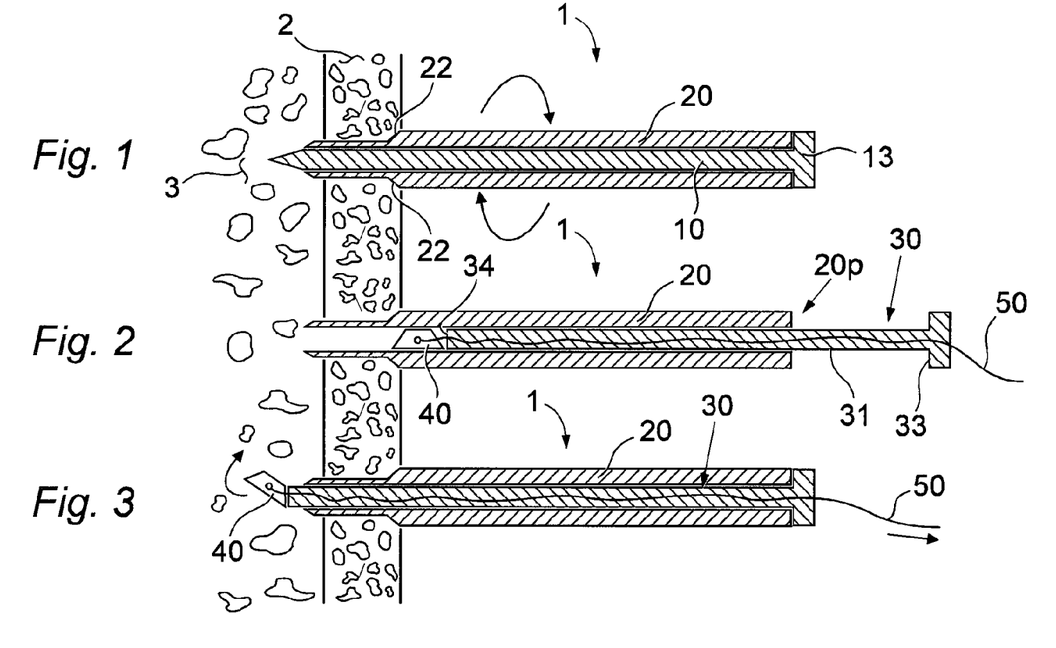
FIGS. 1-3 are side sectional views of a tissue anchor insertion system showing sequential steps in the insertion of a tissue anchor into a bone.

The drill stem 10 is adapted to pass into the bore 25 of the drill sleeve 20 with the cutting bit 12 being initially offered to the bore 25 at the proximal end 20*p* of the sleeve. When the flanged head 13 on the proximal end 10*p* of the drill stem 10 engages the end face of the proximal end 20*p* of the sleeve, the cutting bit 12 on the distal end 10*d* of the drill stem 10 is protruding slightly from the distal end 20*d* of the drill sleeve 20, as is best shown in FIG. 1. The engagement of the head 13 on the distal end 20*d* thereby restricts further axial travel of the drill stem 10 within the drill sleeve 20.

Typically the drill stem 10 and the drill sleeve 20 are keyed together for example, by a bayonet or other fitting (not shown) so that torque is transmitted between them.

A tissue anchor 40 is offered to the bore at the proximal end of the drill sleeve 20*p*, followed by a delivery device in the form of a pusher 30 which supports the anchor 40 within the bore 25 against falling back to the proximal end 20*p*. The anchor 40 has a cross section that is typically in the form of a rhombus or other shape, and typically has a long side 41 that is longer than the outer diameter of the drill sleeve 20, so that the anchor can only fit into the bore when the long side 41 of the anchor 40 is parallel to the axis of the bore. The anchor 40 can have a suture 50 attached through a choice of anchor holes 42, 43, which are typically arranged eccentrically in the anchor 40 so that tension on the suture 50 pulls the anchor in a non-symmetrical manner. However, symmetrical designs of anchor (e.g. anchors 45 and 48) can work satisfactorily provided normally that their length has a greater dimension than the (outer) diameter of the drill sleeve 20. The pusher 30 typically has a shaft 31 and a flanged head 33. The shaft 31 can have a cross section that is received within the bore 25, but typically incorporates cutaway sections, for example in the form of a square or oval, so that spaces are created between the non-cylindrical shaft 31 and the cylindrical bore 25 to accommodate the sutures 25 trailing behind the anchor 40.

In use, the drill stem 10 is inserted into the bore 25 in the drill sleeve 20 by initially offering the cutting bit 12 to the bore at the proximal end 20d of the drill sleeve 20 and sliding the drill stem 10 through the bore from the proximal to the distal end of the drill sleeve 20 until the flanged head 13 abuts the proximal end 20p. At this point the cutting bit 12 is only just protruding from the distal end 20d of the sleeve, and the slope between the cutting head 12 and the angled end face 24 of the sleeve is substantially continuous. At this point the drill stem 10 is also typically keyed to the drill sleeve 20. The drill stem and sleeve are then pushed into and through the cortical bone 2 until the cutting head 12 and the distal end face 24 penetrate through the cortical bone 2 and into the cancellous bone 3 beyond it. Optionally the sleeve and the drill stem can be driven in rotation to assist the penetration, which is typically useful if the drill stem or the sleeve have cutting formations such as teeth or spiral formations adapted to drill or cut through the bone. The drill sleeve 20 and drill stem 10 are pushed through the cortical bone 2 until the neck 23 has penetrated the cortical bone 2 and the shoulder 22 abuts against the outer surface of the cortical bone 2. At this point, rotation is useful to abrade the outer surface of the hole in the bone 2 that is occupied by the neck 23, and the shoulder 22 optionally carries abrading formations to smooth the edge of the hole and reduce the risk of subsequent damage to the suture 50. Once the neck 23 has been embedded in the cortical bone, the drill stem 10 is withdrawn from the bore 25 at the proximal end 20p, leaving the drill sleeve 20 in place within the tissue and providing a work channel through the bore 25 so that the tissue anchor 40 can be inserted into the bore 25 at the proximal end 20p, followed by the pusher 30. Optionally the tissue anchor can be restrained on the delivery device, but in this example, the two are offered to the bore 25 separately, and the pusher 30 pushes the anchor 40 ahead of it through the bore 25, and supports it against axial travel back toward the proximal end 20p. The square cross section of the shaft 31 of the pusher 30 means that the sutures 50 trailing behind the anchor 40 in the bore 25 are accommodated in the spaces between the shaft 31 and the bore 25, and do not interfere with the movement of the pusher 30. The pusher 30 pushes the anchor through the work channel from the outer proximal end 20p to the inner distal end 20d where the anchor is to be deployed.

The shaft 31 of the pusher 30 has a similar length to the drill stem, so when the flanged head 33 of the pusher 30 abuts against the proximal end of the drill sleeve 20d, the distal end of the pusher has emerged from the bore and has pushed the anchor 40 fully out of the bore 25 and into the cancellous bone 3 in the area in which it is to be deployed.

The angle of the end face 34 of the pusher 30 is typically non-identical with a short side 44 of the anchor 40. In this example, there is a 30 degree variance between the two. When the anchor 40 is confined within the bore 25 and is being pushed by the pusher 30, it cannot move out of its insertion configuration shown in FIG. 2, in which the long sides are each parallel to the main axis of the bore 25. However, when the anchor is pushed out of the distal end 20d of the drill sleeve 20, the anchor is no longer restrained in the insertion configuration and is rotated by the mismatched angles on end face 34 and short side 44, as is best shown in FIG. 3. At this point, tension on the suture 50 and the eccentricity of the connection between the suture 50 and the anchor enhances such rotation. This moves the anchor 40 into a set configuration in which it is no longer able to pass through the bore 25 or the hole made by the neck 23, and is therefore anchored within the cancellous bone, on the inner face of the cortical bone 2.

At this point, the pusher 30 and drill sleeve 20 are withdrawn from the bone 2, passing over the suture 50, leaving a hole with a diameter that is substantially the same as the outer diameter of the neck 23, and with an abraded smooth outer rim, which is less likely to snag the suture. The adoption of the set configuration means that the long edge of the anchor 40 is unable to pass into the hole, and is anchored in the bone 2. The suture 50 can then be tied to a ligament or other tissue as normal.

Typically the neck 23 is slimmer than the body of the drill sleeve 20 so that the hole created by the sleeve in the bone is as small as possible, and so that the anchor 40 has less chance of passing back through the hole after insertion. The bore 25 is typically as large as possible, to accommodate large designs of anchor. Therefore, the walls of the neck 23 are typically as thin as possible.

The drill stem and/or the sleeve can be made from metal and can be sterilised and re-used, or can be disposable single use items.

FIG. 18 shows an end view of an alternative design of anchor 45 that can be used with the same system, which is generally brick-shaped, with a square cross section, but with an axial length that is longer than the outer diameter of the neck 23. FIG. 19 shows another alternative design of anchor 48 that is also brick shaped, with an oval cross section, that is retained in a particular configuration in the tubular bore by the major diameters of the anchor engaging the inner surface of the bore 25, but with the minor diameters creating spaces between the anchor and the bore for the emergence of the suture 50 from the sides of the anchor 48. A choice of suture tracks 46, 47, 49 are provided through the anchors 45, 48. These can be eccentric if desired.

Figure 10:
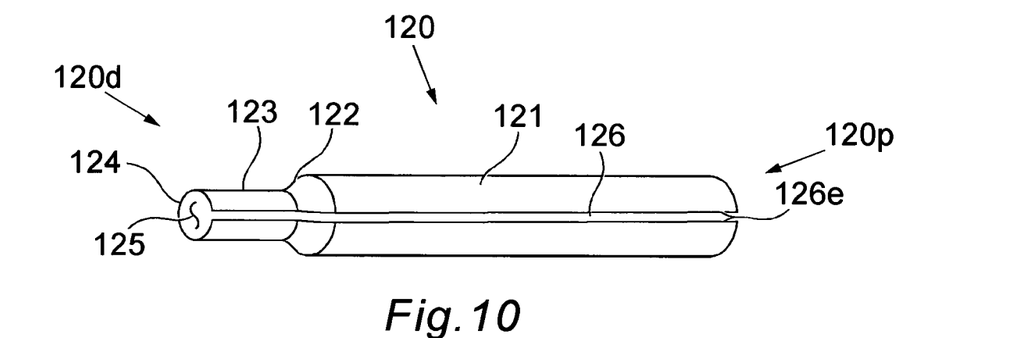
FIG. 10 is a perspective view of a second sleeve.

A further design of sleeve 120 is shown in FIG. 10. The sleeve 120 is again in the form of a drill sleeve typically differs from previous embodiments in the design of drill stem 110 and drill sleeve 120. Other features that are shared between the different embodiments will not be described in detail. The drill sleeve 120 has a slot 126 extending along the length of the sleeve, from the proximal end 120p to the distal end 120d. The slot 126 permits the sleeve to slide sideways over sutures 50, and so facilitates the assembly of the system without threading all components through the bore 125. One or both of the edges 126e of the slot 126 can be formed to extend radially inward (e.g. in a curl) so as to avoid damage to the bone tissue when the sleeve is rotated during insertion.

Figure 12:
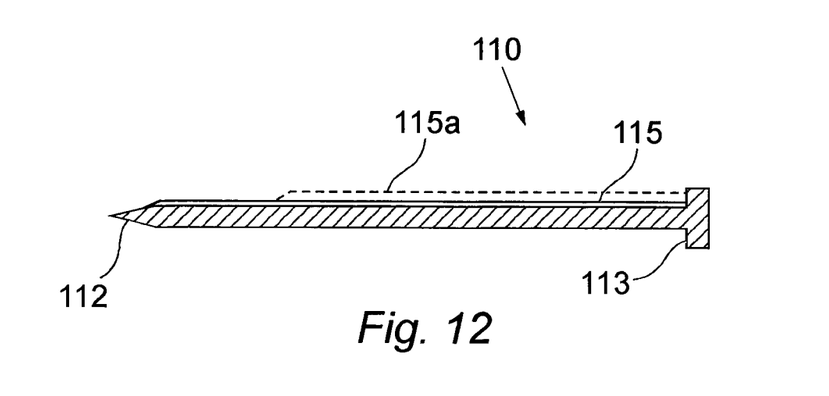
FIG. 12 is a perspective view of a second cutting device for use with the FIG. 10 sleeve.

The drill stem 110 shown in FIG. 12 is adapted for use with the drill sleeve 120. The drill stem 110 has a spline 115 extending along its length between the flanged head 113 and the cutting bit 112, terminating just short of the cutting bit. The spline 115 engages the slot 126 in the sleeve, rotationally locking the two together. Optionally, the spline can have a raised portion 115a that follows the line of the outer surface of the drill sleeve 120 as the shoulder 122 extends radially away from the neck 123, so that the whole of the slot 126 is substantially occluded by the spline 115a to prevent damage to the bone tissue when the sleeve is rotated during insertion. The spline 115 keys the drill stem 110 to the drill sleeve 120 to transmit torque. The drill sleeve 120 can optionally have serrations on its leading edge to drill into the tissue. Alternatively, or additionally, the leading end can have a sharpened ridge to cut into the tissue.

Figure 4:
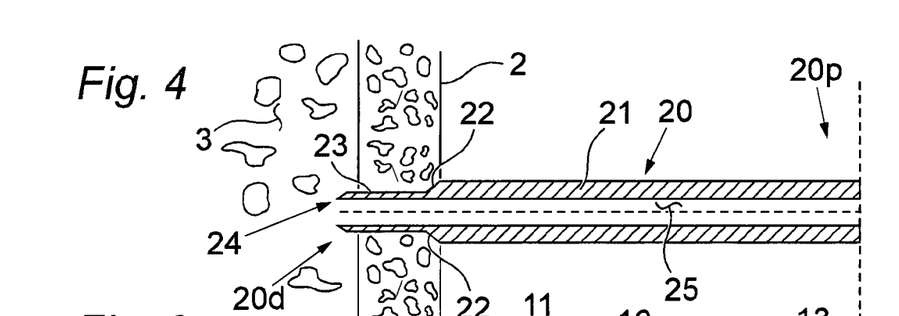
FIG. 4 is a side sectional view of a sleeve of the tissue anchor insertion system.
Figures 5, 7:
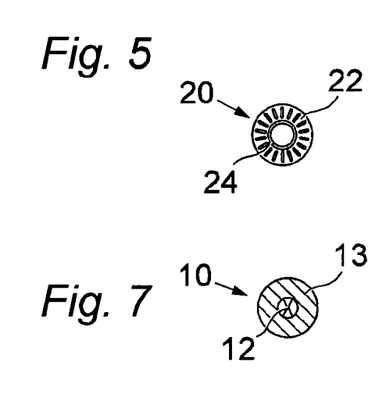
FIG. 5 is an end view of the FIG. 4 sleeve viewed from the tip.
FIG. 7 is an end view of the FIG. 5 cutting device viewed from the tip.
Figures 6, 8:
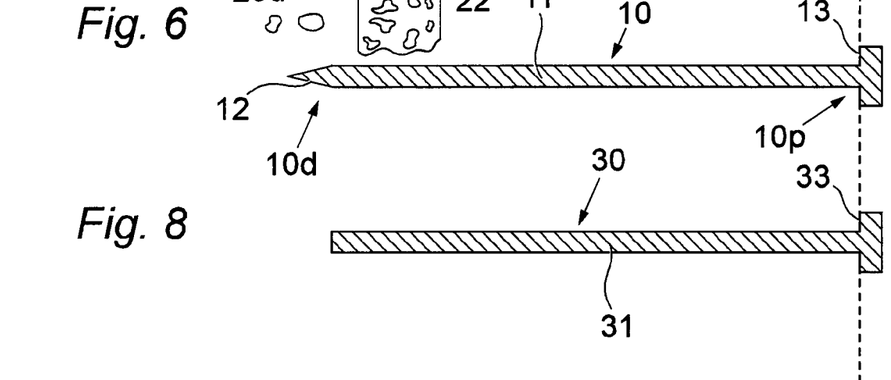
FIG. 6 is a side sectional view of a cutting device of the tissue anchor insertion system.
FIG. 8 is a side sectional view of a delivery device of the tissue anchor insertion system.
Figure 9:
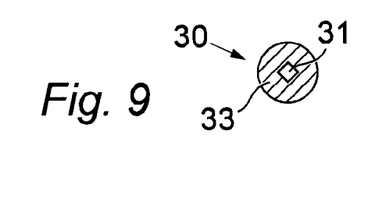
FIG. 9 is an end view of the FIG. 8 delivery device viewed from the tip.
Figure 11:
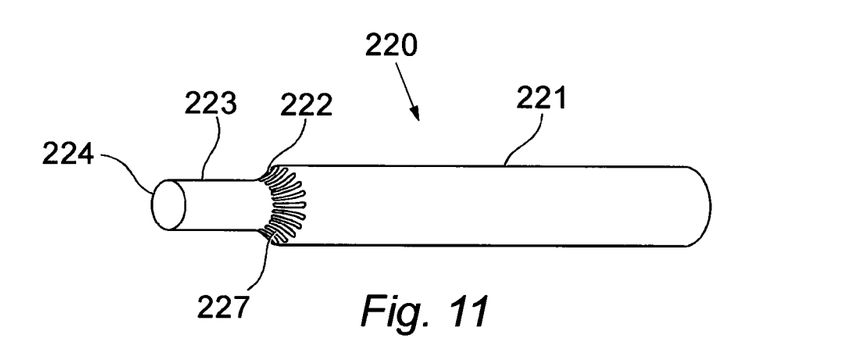
FIG. 11 is a perspective view of a third sleeve.

A further design of sleeve 220 is shown in FIG. 11. The sleeve 220 differs in the design of drill stem 210 and sleeve 220. Other features that are shared between the different embodiments will not be described in detail. The sleeve 220 is in the form of a drill sleeve and has raised abrading formations 227 on the outer surface of the shoulder 222, so that when the neck 223 is penetrating the bone tissue as shown in FIG. 4, for example, the abrading formations smooth out the sharp edges on the outer surface of the hole in the bone 2, so that when the drill sleeve 220 is withdrawn from the hole after insertion of the anchor 40, the suture 50 does not become damaged or snagged on the edges of the hole through the bone. The abrading formations 227 can be rough or fine in texture, and can typically follow the contours of the shoulder. The drill sleeve 220 can optionally have serrations on its leading edge to drill into the tissue. Alternatively, or additionally, the leading end can have a sharpened ridge to cut into the tissue.

Figures 13, 14:
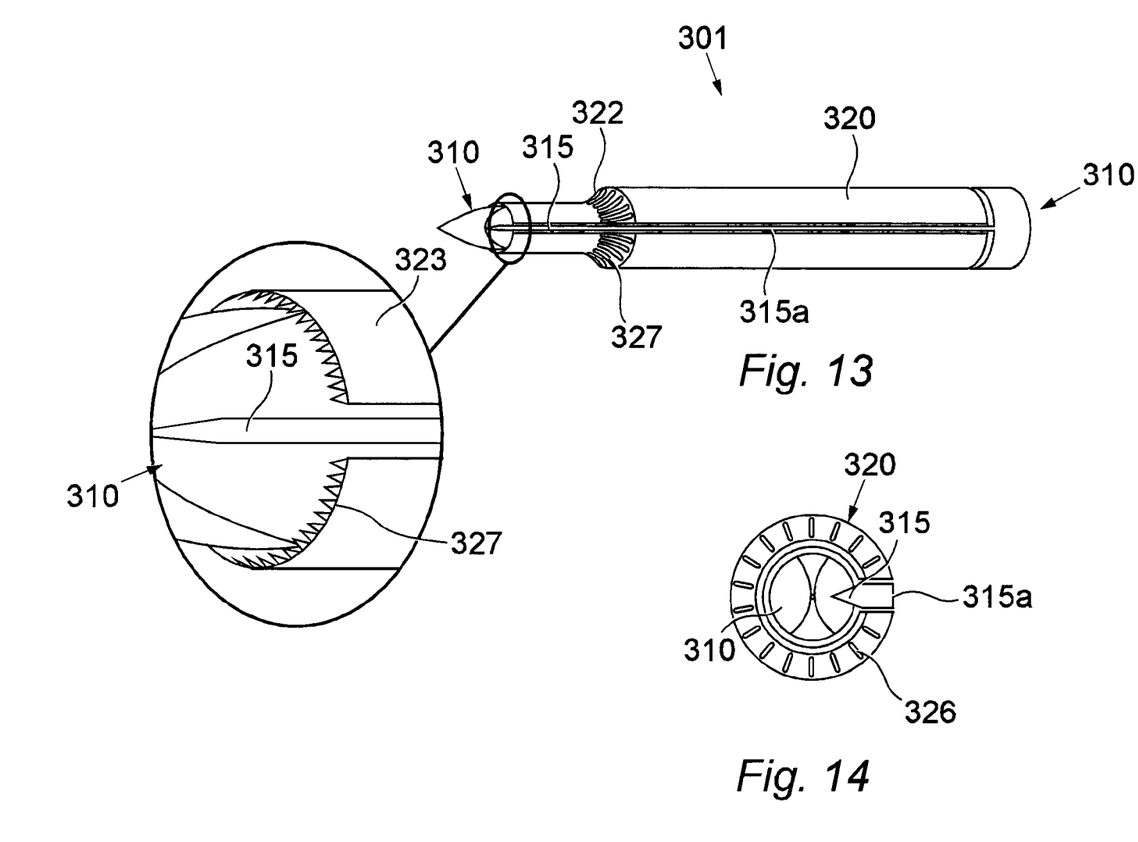
FIG. 13 is a perspective view of an assembled third sleeve and third cutting device.
FIG. 14 is an end view of FIG. 13.
Figure 15:
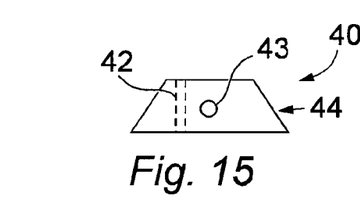
FIGS. 15-17 show first, second and third designs of anchor.
Figure 16:
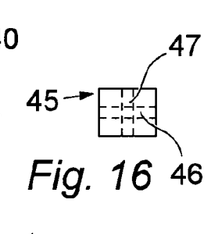
Figure 17:
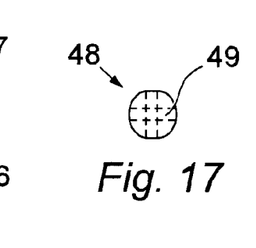

FIG. 13 and FIG. 14 show a further embodiment of a system 301, with a sleeve 320 having a slot 326, a drill stem 310 having a spline 315 with a low neck portion and a raised body portion 315a a previously described, and with abrading formations 327 on the outer surface of the shoulder 322. The spline 315 can optionally extend radially outward beyond the outer surface of the sleeve 320, and can optionally be hardened at the distal end of the drill stem 310 to make the hole slightly larger than the drill sleeve 320, thereby facilitating withdrawal of the sleeve from the bone after insertion of the anchor 40. The neck 323 of the drill sleeve 320 has serrations 327 on its leading edge to cut into the bone (shown in the insert to FIG. 13). This feature can be provided on other embodiments described.

The embodiments in FIGS. 10-14 optionally use the same design of pusher 30 as previously described. Embodiments of the invention permit more certainty in the creation of the aperture for insertion of the anchor and for emergence of the suture, and the insertion of the sleeve into the bone creates the tunnel required for the passage of the anchor into the tissue and establishes a guide path for the insertion of the anchor into the correct place. The optional provision of a bevel on the anchor facilitates the configuration change of the anchor after emergence from the bore of the sleeve. The cutter device or the sleeve can have threads adapted to drive the components into the tissue if desired.

Modifications and improvements can be incorporated without departing from the scope of the invention.

The invention claimed is:

1. A tissue anchor insertion system for inserting a tissue anchor into a body tissue, the system comprising:
a cutting device having a sharp leading end configured to create an aperture in a body tissue for insertion of the tissue anchor therein;
a sleeve having proximal and distal ends and having a bore through the sleeve, extending between the proximal and distal ends, and a tissue anchor delivery device configured to support the tissue anchor during insertion of the tissue anchor into the tissue;
wherein at least one of the cutting device and the sleeve has a shoulder to engage the other in order to transmit axial forces between the cutting device and the sleeve;
wherein during creation of the aperture in the tissue, the cutting device is adapted to be received within bore of the sleeve and is adapted to extend at least partially from a distal end of the bore at the distal end of the sleeve;
wherein the shoulder engages when the cutting device is inserted into the bore of the sleeve and the sharp leading end of the cutting device extends from the distal end of the sleeve;
wherein engagement of the shoulder limits the extension of the sharp leading end of the cutting device from the distal end of the sleeve, such that when the shoulder is engaged, the cutting device extends from the distal end of the sleeve by a distance determined by a position of the shoulder;
wherein the distal end of the sleeve is configured to penetrate the tissue in which the tissue anchor is to be inserted; and
wherein during insertion of the tissue anchor the sleeve is configured to accommodate the tissue anchor and the delivery device within the bore of the sleeve and to allow passage of the tissue anchor through the distal end of the bore, wherein
the sleeve has a slot along a length of the sleeve from the proximal end to the distal end, extending through the sleeve to permit passage of sutures through the slot between the bore of the sleeve and an external surface of the sleeve, and wherein the slot on the sleeve is at least partially occluded by a spline on the cutting device.

2. A system as claimed in claim 1, wherein the distal end of the sleeve has at least one angled end face.

3. A system as claimed in claim 1, wherein the distal end of the sleeve and the leading end of the cutting device taper at the same angle with respect to the long axis of the sleeve.

4. A system as claimed in claim 1, wherein the sleeve incorporates cutting formations to cut the tissue in which the tissue anchor is to be inserted.

5. A system as claimed in claim 4, wherein the cutting formations comprise serrations located on the end face of the sleeve.

6. A system as claimed in claim 1, wherein the walls of the leading end of the sleeve converge at the distal tip of the sleeve to a ridge configured to cut into the tissue.

7. A system as claimed in claim 1, wherein the delivery device is configured to extend beyond the distal end of the sleeve, to space the anchor away from the distal end of the sleeve during configuration changes of the anchor in the tissue.

8. A system as claimed in claim 1, wherein the delivery device and/or the sleeve have graduation marks indicating the depth of insertion of the delivery device within the sleeve.

9. A system as claimed in claim 1, wherein the cutting device and the sleeve are rotationally connected together to transmit torque between them.

10. A system as claimed in claim 1, wherein the cutting device supports the inner wall of the sleeve along at least a part of the leading end tip of the sleeve.

11. A system as claimed in claim 1, wherein at least one of the edges of the slot is formed by a face of the sleeve being curled to extend radially inwards toward the axis of the sleeve.

12. A system as claimed in claim 1, wherein the cutting device comprises an axial shaft, with a cutting formation that extends radially with respect to the axial shaft, wherein the cutting formation is configured to extend through the slot in the sleeve, and extends radially beyond the outer surface of the sleeve, in order to cut into the tissue to form the aperture for passage of the sleeve and the cutting device into the tissue.

13. A system as claimed in claim 1, wherein the leading end of the cutting device occludes the distal end of the sleeve when the leading end of the cutting device extends through the distal end of the sleeve, whereby the tissue being penetrated is excluded from the bore of the sleeve.

14. A system as claimed in claim 1, wherein the sleeve is stepped to form an external formation extending radially from the sleeve to limit the passage of the sleeve into the tissue.

15. A system as claimed in claim 14, wherein the external formation faces the leading end and is spaced therefrom, and incorporates an abrading formation to abrade the outer surface of the aperture made by the sleeve through the tissue.

16. A system as claimed in claim 1, incorporating a handle for connection to the cutting device and/or the sleeve, and wherein the cutting device and/or the sleeve has a formation at its proximal end to facilitate connection with the handle for manipulating the cutting device and/or the sleeve.

17. A system as claimed in claim 1, wherein the tissue anchor delivery device has a fulcrum on its distal tip to engage the tissue anchor, wherein the fulcrum is configured to support the tissue anchor only when the tissue anchor is contained within the bore of the sleeve.

18. A system as claimed in claim 1, wherein at least one channel is formed between the delivery device and the sleeve for accommodation of sutures in the channel.

19. A system as claimed in claim 1, wherein the anchor is formed from a material that is inherently adapted to change its shape after insertion of the anchor into the tissue.

20. A system as claimed in claim 1, wherein the anchor has axial channels in or on the anchor said axial channels being configured to accommodate sutures.

21. A system as claimed in claim 1, wherein the anchor is maintained within the sleeve in an insertion configuration during passage of the anchor through the sleeve.

22. A method of inserting a tissue anchor into a tissue, the method comprising:
    providing a cutting device having a sharp leading end configured to create an aperture in a body tissue for insertion of a tissue anchor therein;
    inserting the cutting device into the bore of a sleeve having an open end, the sleeve having a slot extending through the sleeve along the length of the sleeve from a proximal end to a distal end;
    occluding the slot on the sleeve along its length by a spline on the cutting device;
    inserting the cutting device and the open end of the sleeve into the tissue;
    mounting the tissue anchor on a delivery device;
    inserting the tissue anchor and the delivery device into the bore of the sleeve;
    moving the delivery device relative to the sleeve to urge the tissue anchor out of the open end of the sleeve and into the surrounding tissue bore; and
    wherein the method includes passing sutures through the slot between the bore of the sleeve and the external surface of the sleeve.

23. A method as claimed in claim 22, wherein the cutting device and the open end of the sleeve are inserted into the tissue to a depth at which the open end of the sleeve corresponds to the desired depth of insertion of the tissue anchor and wherein the cutting device is removed from the sleeve while the sleeve remains at the said depth, and wherein the delivery device and the tissue anchor are inserted through the sleeve to deliver the tissue anchor from the open end of the sleeve at the said depth of insertion.

24. A method as claimed in claim 22, wherein the distal end of the sleeve is pushed through the aperture created by the cutting device, so that the leading end of the sleeve is embedded within the tissue in which the tissue anchor is to be delivered when the tissue anchor emerges from the distal end of the sleeve.

25. A method as claimed in claim 22, wherein the sleeve cuts part of the aperture through the tissue.

26. A method as claimed in claim 22, wherein the tissue anchor is inserted into a proximal end of the sleeve and is pushed through the sleeve in a first insertion configuration and wherein the tissue anchor emerges from the distal end of the sleeve and adopts a second anchoring configuration when embedded in the tissue.

27. A method as claimed in claim 22, wherein the cutting device is removed from the bore of the sleeve prior to inserting the tissue anchor and the delivery device into the bore.

28. A method as claimed in claim 22, wherein the sleeve is maintained in place in the tissue during removal of the cutting device and during insertion of the delivery device and the tissue anchor, and is withdrawn from the tissue after the tissue anchor has been inserted.

29. A method as claimed in claim 22, wherein the sleeve has a proximal and a distal end and wherein the bore extends between the proximal and distal ends of the sleeve, and wherein the cutting device and the delivery device and the tissue anchor are initially inserted into the bore of the sleeve at the proximal end of the sleeve, and wherein the tissue anchor passes through the bore from one end of the sleeve to the other while the sleeve is inserted in the tissue.

30. A method as claimed in claim 22, wherein the delivery device spaces the anchor away from the end of the sleeve during setting of the anchor.

31. A tissue anchor insertion system for inserting a tissue anchor into a body tissue, the system comprising:
    a cutting device having a sharp leading end configured to create an aperture in a body tissue for insertion of the tissue anchor therein;
    a sleeve having proximal and distal ends and having a bore through the sleeve, extending at least partially between the proximal and distal ends, and a tissue anchor delivery device configured to support the tissue anchor during insertion of the tissue anchor into the tissue;
    wherein at least one of the cutting device and the sleeve has a shoulder to engage the other in order to transmit axial forces between the two components;
    wherein during creation of the aperture in the tissue, the cutting device is adapted to be received within bore of the sleeve and is adapted to extend at least partially from a distal end of the bore at the distal end of the sleeve;
    wherein the shoulder engages when the cutting device is inserted into the bore of the sleeve and the sharp leading end of the cutting device extends from the distal end of the sleeve;
    wherein the engagement of the shoulder limits the extension of the sharp leading end of the cutting device from the distal end of the sleeve, such that when the shoulder is engaged, the cutting device extends from the distal end of the sleeve by a distance determined by the position of the shoulder;
    wherein the distal end of the sleeve is configured to penetrate the tissue in which the tissue anchor is to be inserted; and
    wherein during insertion of the tissue anchor the sleeve is configured to accommodate the tissue anchor and the delivery device within the bore of the sleeve and to allow passage of the tissue anchor through the distal end of the bore; and
    wherein the sleeve has a slot along the length of the sleeve from the proximal end to the distal end, extending through the sleeve to permit passage of sutures through the slot between the bore of the sleeve and the external surface of the sleeve, and wherein the slot on the sleeve is occluded along the length of the slot by a spline on the cutting device.

32. A tissue anchor insertion system for inserting a tissue anchor into a body tissue, the system comprising:
    a cutting device having a sharp leading end configured to create an aperture in a body tissue for insertion of the tissue anchor therein;
    a sleeve having proximal and distal ends and having a bore through the sleeve, extending between the proximal and distal ends, and a tissue anchor delivery device configured to support the tissue anchor during insertion of the tissue anchor into the tissue;
    wherein during creation of the aperture in the tissue, the cutting device is adapted to be received within bore of the sleeve and is adapted to extend at least partially from a distal end of the bore at the distal end of the sleeve, the cutting device and the sleeve being connected by a bayonet connection;
    wherein the distal end of the sleeve is configured to penetrate the tissue in which the tissue anchor is to be inserted;
    wherein during insertion of the tissue anchor the sleeve is configured to accommodate the tissue anchor and the delivery device within the bore of the sleeve and to allow passage of the tissue anchor through the distal end of the bore; and
    wherein the sleeve has a slot along the length of the sleeve from the proximal end to the distal end, extending through the sleeve to permit passage of sutures through the slot between the bore of the sleeve and the external surface of the sleeve, and wherein the slot on the sleeve is at least partially occluded by a spline on the cutting device.

33. A tissue anchor insertion system for inserting a tissue anchor into a body tissue, the system comprising:
    a cutting device having a sharp leading end configured to create an aperture in a body tissue for insertion of the tissue anchor therein;
    a sleeve having proximal and distal ends and having a bore through the sleeve, extending at least partially between the proximal and distal ends, and a tissue anchor delivery device configured to support the tissue anchor during insertion of the tissue anchor into the tissue;
    wherein during creation of the aperture in the tissue, the cutting device is adapted to be received within bore of the sleeve and is adapted to extend at least partially from a distal end of the bore at the distal end of the sleeve, the cutting device and the sleeve being connected by a bayonet connection;
    wherein the distal end of the sleeve is configured to penetrate the tissue in which the tissue anchor is to be inserted;
    wherein during insertion of the tissue anchor the sleeve is configured to accommodate the tissue anchor and the delivery device within the bore of the sleeve and to allow passage of the tissue anchor through the distal end of the bore; and
    wherein the sleeve has a slot along the length of the sleeve from the proximal end to the distal end, extending through the sleeve to permit passage of sutures through the slot between the bore of the sleeve and the external surface of the sleeve, and wherein the slot on the sleeve is occluded along the length of the slot by a spline on the cutting device.

* * * * *